(12) United States Patent
Calicott et al.

(10) Patent No.: US 7,520,188 B2
(45) Date of Patent: Apr. 21, 2009

(54) METHOD FOR CONTROLLING QUALITY OF A FIBERGLASS MAT

(75) Inventors: John M. Calicott, Fort Smith, AR (US); Donald E. Wise, Jr., Newark, OH (US)

(73) Assignee: OCV Intellectual Capital, LLC DE (US)

( * ) Notice: Subject to any disclaimer, the term of this patent is extended or adjusted under 35 U.S.C. 154(b) by 98 days.

(21) Appl. No.: 11/805,614

(22) Filed: May 24, 2007

(65) Prior Publication Data

US 2008/0289409 A1 Nov. 27, 2008

(51) Int. Cl.
*G01N 33/34* (2006.01)

(52) U.S. Cl. ............... 73/865.8; 356/402; 382/141; 702/81; 702/84

(58) Field of Classification Search .......... 73/865.8; 382/11, 141; 356/402; 702/81, 82, 83, 84
See application file for complete search history.

(56) References Cited

U.S. PATENT DOCUMENTS

| | | | | |
|---|---|---|---|---|
| 3,445,656 A | * | 5/1969 | Hull et al. | 250/461.1 |
| 3,448,268 A | * | 6/1969 | Proctor | 250/353 |
| 3,524,983 A | * | 8/1970 | Voelz | 250/341.6 |
| 3,604,812 A | * | 9/1971 | Walsen | 356/402 |
| 4,310,248 A | * | 1/1982 | Meredith | 356/402 |
| 4,363,968 A | * | 12/1982 | McGowan et al. | 250/339.1 |
| 4,582,520 A | | 4/1986 | Sturm | |
| 4,609,628 A | | 9/1986 | Aschenbeck | |
| 4,684,244 A | * | 8/1987 | Butts et al. | 356/39 |
| 4,769,544 A | * | 9/1988 | Dahlquist | 250/339.12 |
| 5,142,151 A | | 8/1992 | Varnell et al. | |
| 5,457,319 A | | 10/1995 | Moe et al. | |
| 5,596,025 A | * | 1/1997 | Oxman et al. | 523/109 |
| 5,633,722 A | * | 5/1997 | Wasinger et al. | 356/402 |
| 6,099,162 A | * | 8/2000 | Walsh | 374/30 |
| 6,373,519 B1 | * | 4/2002 | Sybert et al. | 348/86 |
| 6,991,940 B2 | * | 1/2006 | Carroll et al. | 436/514 |
| 7,063,983 B2 | | 6/2006 | Chen | |
| 7,197,177 B2 | * | 3/2007 | Lowe | 382/141 |
| 2001/0049083 A1 | * | 12/2001 | Jung et al. | 433/29 |
| 2003/0071998 A1 | * | 4/2003 | Krupka et al. | 356/402 |
| 2003/0190578 A1 | * | 10/2003 | Lehmann | 433/26 |
| 2004/0173671 A1 | * | 9/2004 | Ferraro | 235/379 |
| 2004/0190367 A1 | * | 9/2004 | Wierzbicki et al. | 366/140 |

FOREIGN PATENT DOCUMENTS

DE 19637234 A1 * 3/1998

\* cited by examiner

*Primary Examiner*—David A. Rogers
(74) *Attorney, Agent, or Firm*—James J. Dottavio; Kathryn W. Grant

(57) ABSTRACT

A method is provided for controlling the quality of a fiberglass mat. The method includes the steps of dyeing a test specimen of the fiberglass mat, scanning the test specimen with an optical detector to collect color data and comparing the color data to a predetermined standard to determine if the fiberglass mat is within the desired product specification.

17 Claims, 1 Drawing Sheet

METHOD FOR CONTROLLING QUALITY OF A FIBERGLASS MAT

TECHNICAL FIELD AND INDUSTRIAL APPLICABILITY OF THE INVENTION

The present invention relates generally to a method for controlling the quality of a fiberglass mat and, more particularly, to a method for determining the extent or level of cure of a fiberglass mat.

BACKGROUND OF THE INVENTION

Fiberglass mats are made from fiberglass and a polymer binder which is applied to hold the mat together. The fiberglass may take the form of a continuous strand or staple fibers that are cut and chopped to a desired length. Typically the fiberglass is deposited onto a moving belt where a binder is applied. The materials are then cured in an oven at a predetermined curing temperature for a predetermined curing time in order to bind the glass fibers together and provide the mat with consistent shape.

In order to be useful for its intended purpose, the fiberglass mat must be characterized by specified properties. The level of cure provided in the fiberglass mat determines a great many of these properties. As a consequence, good quality control requires the manufacturer to monitor and maintain a proper level of cure in a fiberglass mat product. Toward this end, a number of methods have been utilized to allow the manufacturer to monitor and determine the level of cure in a fiberglass mat product.

U.S. Pat. No. 7,063,983 to Chen discloses a method for determining cure in a polycarboxylic acid bindered material that uses a solution which indicates the degree of cure based on the color the solution turns after being sprayed upon the article.

U.S. Pat. No. 4,609,628 to Ashtenbeck discloses a method for determining binder content and degree of cure in a fibrous mat utilizing electromagnetic radiation.

U.S. Pat. No. 4,582,520 to Sterm and U.S. Pat. No. 5,457,319 to Moe et al disclose processes for measuring a degree of cure through the use of infrared radiation.

It is also known to utilize what is referred to in the art as the "red dye test" in order to determine the level of cure in a fiberglass mat. In accordance with the state of the art red dye test, a test sample is cut from a finished roll of fiberglass mat. The sample is then submerged into a red dye bath to ensure that it is completely saturated with the dye. The sample is then rinsed with fresh water. Excess water is then removed from the sample. The sample is then visually compared to a predetermined standard to determine if the finished mat is within specification.

The present invention relates to a new and improved method for controlling quality of a fiberglass mat that is more accurate and efficient than the state of the art red dye test.

SUMMARY OF THE INVENTION

In accordance with the purposes of the present invention as described herein, a method is provided for controlling the quality of a fiberglass mat. The method comprises the step of dyeing a test specimen of the fiberglass mat. Next is the scanning of that test specimen with an optical detector to collect color data and storing that color data in a memory device. This is followed by using a computing system to compare the color data to a predetermined standard also stored in the memory device to determine if the fiberglass mat is within desired product specification.

More specifically, the method includes the cutting of a test specimen from the fiberglass mat following curing of the fiberglass mat and prior to dyeing. Preferably, the test specimen is cut across the entire width of the fiberglass mat. This is followed by the submerging of the test specimen in a red dye bath. Next is the rinsing of the test specimen with water to remove excess dye. This is followed by removing the water from the test specimen prior to scanning.

The method further includes the steps of placing the test specimen on a scanner at a particular, predetermined point. Specifically the method may include outlining a box on the scanner to indicate the particular predetermined point at which any test specimen is to be positioned.

In accordance with additional aspects of the present invention the method may further include adjusting parameters for processing the fiberglass mat based upon the comparison of the collected color data to the predetermined standard.

More particularly describing the invention the method includes distinguishing red, green and blue pixels in a scan image of the test specimen. Further, the method includes determining a ratio of red pixels to the total number of pixels in the scan image. That ratio is then used to determine the level of cure of the test specimen.

In addition, the method includes establishing a scale representing different cure levels of the fiberglass mat. This is accomplished by scanning samples of the fiberglass mat having known levels of cure and determining the ratio of red pixels to the total number of pixels for the known levels of cure. The method then includes comparing the ratio of red pixels to the total number of pixels in the scan image to this scale whereby the scale is used as the predetermined standard. In accordance with yet another aspect, the method includes rating the cure level of a test specimen wherein Rating #1 corresponds to 0-3% red pixels, Rating #2 corresponds to 3-7% red pixels, Rating #3 corresponds to 7-11% red pixels, Rating #4 corresponds to 11-18% red pixels and Rating #5 corresponds to 18-100% red pixels.

In the following description there is shown and described the preferred embodiment of the present invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawing incorporated herein and forming a part of the specification, illustrates several aspects of the present invention and together with the description serves to explain certain principles of the invention. In the drawing.

DETAILED DESCRIPTION AND PREFERRED EMBODIMENT OF THE INVENTION

Figure 1:
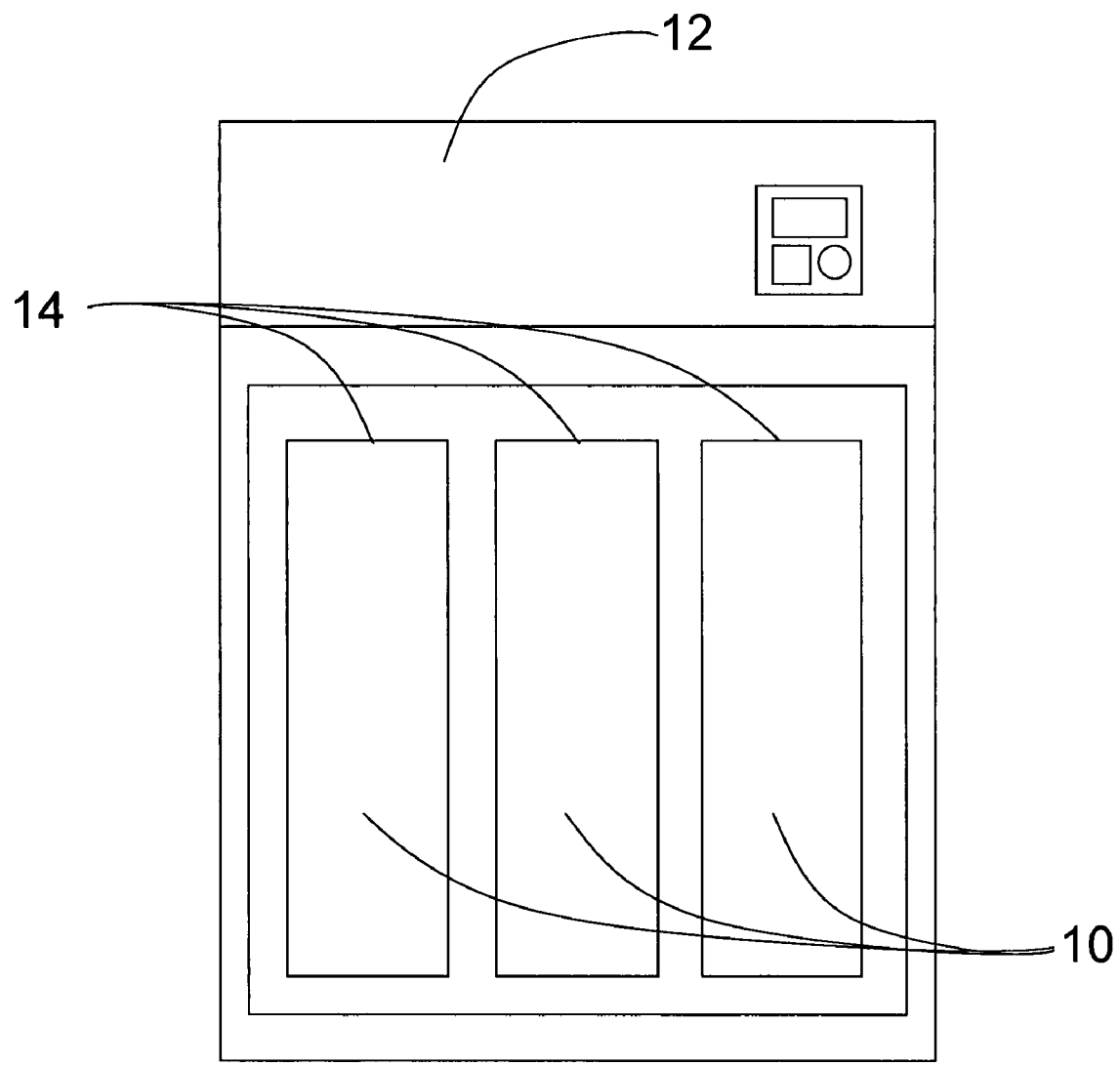
FIG. 1 is a schematical top plan view illustrating how the cut and dyed test specimen is positioned on the scanner in order to collect color data used in controlling the quality of the fiberglass mat.

The present invention relates to a method for controlling the quality of a fiberglass mat. The method being described is particularly useful in controlling the quality of a fiberglass mat that is wet formed from glass fiber and a binder such as urea formaldehyde and acrylic latex. The glass fiber may be of substantially any type including, but not limited to, E-glass, S-glass and R-glass. Continuous glass fiber or staple glass fiber may be utilized.

Typically the binder content of the fiberglass mat is between approximately 16 and approximately 21 weight percent and is made up of approximately 90 percent urea formaldehyde and approximately 10 percent acrylic latex. Further the fiberglass mat typically has a basis weight ranging from approximately 1.02 to approximately 2.56 lbs/csf.

The method for controlling the quality of a fiberglass mat may be generally described as including the steps of dyeing a test specimen of the fiberglass mat, scanning the test specimen with an optical detector to collect color data, storing the collected color data in a memory device and using a computing system to compare that color data to a predetermined standard also stored in the memory device to determine if the fiberglass mat is within a desired product specification. The computing system may comprise a personal computer incorporating a dedicated microchip or running appropriate software to complete the desired comparison. Such a software program includes the software entitled "Red Dye Cure Analysis" owned by the assignee of the present invention.

More specifically, the step of dyeing a test specimen may include the steps of cutting the test specimen from a finished fiberglass mat following curing of the fiberglass mat and prior to drying. For best results, the test specimen is cut across the entire width of the fiberglass mat. The test specimen is then submerged in a red dye bath. Typically the red dye bath is made up of a concentration of 7 ml of red dye to 10,000 ml of water. This is followed by the rinsing of the test specimen with water to remove any excess dye. Next is the removing of water from the test specimen prior to scanning.

The step of scanning the test specimen with an optical detector is illustrated in FIG. 1. More specifically, it includes placing the cut and dyed test specimen 10 on a scanner 12 at a particular, predetermined point to insure the consistency of each scan. More specifically, the method may also include the outlining of a box 14 on the scanner 12 (such as by using a template) to indicate the particular, predetermined point at which any test specimen 10 is to be positioned prior to scanning. Where the test specimen 10 exceeds the width of the scanner 12, the test specimen may be cut into multiple segments 16 and each segment placed in an appropriate box 14 on the scanner 12. This allows the entire width of the test specimen 10 to be scanned simultaneously. To further aid in obtaining consistent readings, each sample is placed on the scanner with the same side up and with leading edge oriented the same.

The comparing of the collected color data to a predetermined standard may be more specifically described as including distinguishing red, green and blue pixels in a scan image of the test specimen, determining the ratio of red pixels to the total number of pixels in the scan image and using that ratio to determine the level of cure of that specimen. More specifically, a scale is established to represent different cure levels of the fiberglass mat. This is done by scanning samples of fiberglass mat having known levels of cure and determining the ratio of red pixels to the total number of pixels for the known levels of cure. The ratio of red pixels to the total number of pixels in the scan image of the test specimen is then compared to the scale and the scale is thereby used as the predetermined standard. If the test specimen is determined to fall within the desired level of cure and thereby fall within desired product specification, no further action is necessary. If on the other hand, the test specimen falls outside the desired specification, the fiberglass mat from which the test specimen was cut is discarded and the parameters for processing the fiberglass mat are adjusted to bring the product within the predetermined standard and desired specification. Typically this involves adjusting the cure temperature of the curing oven. Alternatively, it could involve adjusting the residence time of the product in the oven.

More specifically describing the invention, the range of color spectrum that is identified as a red, green and blue pixel is established. For example a range of about 51 to about 223 may identify a red pixel, a range of about 51 to about 196 may identify a blue pixel and a range of about 51 to about 166 may identify a green pixel. Any pixel falling in more than one range is counted only toward the total number of pixels. Any pixel falling only in the red range is counted both as a red pixel and as one of the total pixels.

Generally, an appropriate scale for a fiberglass mat of the type in question is presented below in Table 1. Rating #1 is the best. Rating #5 is the worst.

TABLE 1

| Cure Rating (Best-to-Worst) | Percentage of Red Pixels to Total Number of Pixels |
|---|---|
| Rating #1 | 0-3% |
| Rating #2 | 3-7% |
| Rating #3 | 7-11% |
| Rating #4 | 11-18% |
| Rating #5 | 18-100% |

The following example is presented to further illustrate the invention, but it is not to be considered as limited thereto.

EXAMPLE 1

Cut a 4" wide cross direction sample from each of the rolls in a full turn up. Sample is various wet formed fiberglass mat ranging in basis weight from 1.02 to 2.56 lbs./csf. Binder content is 16 to 21% and is made up of 90% UF resin and 10% acrylic Latex. Glass fibers are typically 1¼" M fibers but can be other lengths or diameters. Dwell time in the oven is typically 3.8 to 4 sec in a three zone convention gas fire oven. Temperatures in the three oven zones typically will range between 450 and 550 degrees F.

While keeping samples separated by roll, cut each sample into section no longer then 24" in length.

Submerge sample from each roll into the red dye bath insuring to completely saturate the samples. The red dye bath is made up of a concentration of 7 ml red dye to 10,000 ml water.

Rinse the samples in the sink with fresh water.

Let excess water run off the samples and run them over the vacuum Box to remove any remaining water.

Place samples in the scanner such as a Vidar Designer 18 flat bed scanner. The scanner has boxes outlined on the scanning surface to indicate the location that the samples must be placed. The scanner can accommodate any sample size as long as the software is adjusted accordingly. The idea is to scan one entire product at a time. When the product is 67" wide, it may be cut into two 24" pieces and one 19" piece and we can scan the entire product at once.

Use the software to scan and analyze the samples.

Use the results of the analyses to determine if the mat is in specification and make process adjustments accordingly.

The foregoing description of a preferred embodiment of the invention has been presented for purposes of illustration and description. It is not intended to be exhaustive or to limit the invention to the precise form disclosed. Obvious modifications or variations are possible in light of the above teachings. For example, the fiberglass mat test specimen may be scanned with any appropriate scanning device such as a CCD camera, a photodetector, a fiber optic spectrometer or even combinations thereof. The embodiment was chosen and described to provide the best illustrations of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed:

1. A method for controlling quality of a fiberglass mat, comprising:
    dyeing a test specimen of said fiberglass mat;
    scanning said test specimen with an optical detector to collect color data and storing said color data in a memory device; and
    using a computing system to compare said color data stored in said memory device to a predetermined standard stored in said memory device to determine if said fiberglass mat is within desired product specification;
    said method being characterized by establishing a scale representing different cure levels of said fiberglass mat by scanning samples of fiberglass mat having known levels of cure and determining the ratio of red pixels to the total number of pixels for said known levels of cure.

2. The method of claim 1, including adjusting parameters for processing said fiberglass mat based upon comparison of color data to predetermined standard.

3. The method of claim 1, including comparing said ratio of red pixels to the total number of pixels in said scan image to said scale whereby said scale is used as said predetermined standard.

4. The method of claim 3, including rating the cure level of a test specimen wherein;
    Rating #1 corresponds to 0-3% red pixels;
    Rating #2 corresponds to 3-7% red pixels;
    Rating #3 corresponds to 7-11% red pixels;
    Rating #4 corresponds to 11-18% red pixels; and
    Rating #5 corresponds to 18-100% red pixels.

5. The method of claim 1 including cutting said test specimen from said fiberglass mat following curing of said fiberglass mat and prior to dyeing.

6. The method of claim 5, including cutting said test specimen across entire width of said fiberglass mat.

7. The method of claim 5, including submerging said test specimen in a red dye bath.

8. The method of claim 7, including rinsing said test specimen with water to remove excess dye.

9. The method of claim 8, including removing water from said test specimen prior to scanning.

10. The method of claim 9, including placing said test specimen on a scanner at a particular, predetermined point.

11. The method of claim 10, including outlining a box on said scanner to indicate said particular, predetermined point at which any test specimen is to be positioned.

12. The method of claim 11, including adjusting parameters for processing said fiberglass mat based upon comparison of color data to predetermined standard.

13. The method of claim 12, including distinguishing red, green and blue pixels in a scan image of said test specimen.

14. A method for controlling quality of a fiberglass mat, comprising:
    dyeing a test specimen of said fiberglass mat;
    scanning said test specimen with an optical detector to collect color data and storing said color data in a memory device; and
    using a computing system to compare said color data stored in said memory device to a predetermined standard stored in said memory device to determine if said fiberglass mat is within desired product specification;
    said method being characterized by (a) determining a ratio of red pixels to a total number of pixels in a scan image and using said ratio to determine the level of cure of said test specimen and (b) establishing a scale representing different cure levels of said fiberglass mat by scanning samples of fiberglass mat having known levels of cure and (c) determining the ratio of red pixels to the total number of pixels for said known levels of cure.

15. The method of claim 14, including comparing said ratio of red pixels to the total number of pixels in said scan image to said scale whereby said scale is used as said predetermined standard.

16. A method for controlling quality of a fiberglass mat, compromising:
    dyeing a test specimen of said fiberglass mat;
    scanning said test specimen with an optical detector to collect color data and storing said color data in a memory device; and
    using a computing system to compare said color data stored in said memory device to a predetermined standard stored in said memory device to determine if said fiberglass mat is within desired product specification;
    said method being characterized by distinguishing red, green and blue pixels in a scan image of said test specimen.

17. The method of claim 16, including determining ratio of red pixels to the total number of pixels in said scan image and using said ratio to determine level of cure of said test specimen.

* * * * *